(12) United States Patent
Kozuka et al.

(10) Patent No.: US 8,865,456 B2
(45) Date of Patent: Oct. 21, 2014

(54) NUCLEIC ACID COLLECTION DEVICE AND NUCLEIC ACID COLLECTION AMOUNT ESTIMATION METHOD

(75) Inventors: Masahiro Kozuka, Kyoto (JP); Yukihiro Sukawa, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 376 days.

(21) Appl. No.: 13/458,352

(22) Filed: Apr. 27, 2012

(65) Prior Publication Data

US 2013/0112002 A1     May 9, 2013

(30) Foreign Application Priority Data

Apr. 28, 2011  (JP) ................... 2011-102065
Apr. 27, 2012  (JP) ................... 2012-102052

(51) Int. Cl.
| | |
|---|---|
| *C12M 1/00* | (2006.01) |
| *A61B 17/20* | (2006.01) |
| *C12Q 1/68* | (2006.01) |
| *G01N 1/30* | (2006.01) |
| *A61B 10/00* | (2006.01) |

(52) U.S. Cl.
CPC .............. *G01N 1/30* (2013.01); *C13N 15/1003* (2013.01); *A61B 17/205* (2013.01); *C12Q 1/6806* (2013.01); *C12Q 1/6883* (2013.01); *A61B 10/0045* (2013.01)
USPC ................. 435/283.1; 73/864.11; 73/149

(58) Field of Classification Search
CPC ...... C12Q 1/6806; C12Q 1/68; C12Q 1/6844; C12N 15/1003; C12N 15/1017; G01N 1/30; A61B 10/0045; A61B 17/205
USPC ............... 73/149, 864, 864.01–864.25, 64.56
See application file for complete search history.

(56) References Cited

U.S. PATENT DOCUMENTS

| | | | |
|---|---|---|---|
| 8,257,664 B2 * | 9/2012 | Ogusu | 422/501 |
| 2003/0170664 A1 * | 9/2003 | Mori et al. | 435/6 |
| 2008/0275228 A1 * | 11/2008 | Mori et al. | 536/25.41 |
| 2011/0275126 A1 | 11/2011 | Kozuka | |
| 2012/0138051 A1 * | 6/2012 | Curran et al. | 128/201.25 |

FOREIGN PATENT DOCUMENTS

WO     2010/082631 A1     7/2010

* cited by examiner

*Primary Examiner* — Hezron E Williams
*Assistant Examiner* — Marrit Eyassu
(74) *Attorney, Agent, or Firm* — Morgan, Lewis & Bockius LLP

(57) ABSTRACT

The present invention provides a nucleic acid collection device that can estimate the nucleic acid collection amount when collecting nucleic acids from a biological sample containing nucleic acids. The nucleic acid collection device comprises a sucking and discharging unit for sucking in and forcing out a sample containing nucleic acids, a collector for collecting the nucleic acids by sucking in and forcing out the sample using the sucking and discharging unit, a pressure measurer for measuring a discharging pressure when forcing out the sample and a sucking pressure when sucking in the sample, and measuring a differential pressure that is the difference between the discharging pressure and the sucking pressure, and an estimator for estimating the collection amount of nucleic acids collected based on the differential pressure.

20 Claims, 11 Drawing Sheets

NUCLEIC ACID COLLECTION DEVICE AND NUCLEIC ACID COLLECTION AMOUNT ESTIMATION METHOD

CROSS-REFERENCE TO RELATED APPLICATION

This application is based on Japanese Patent Application No. 2011-102065, filed on Apr. 28, 2011, and Japanese Patent Application No. 2012-102052, filed on Apr. 27, 2012, the entire specification, claims and drawings of which are incorporated by reference herein. This application also incorporates by reference U.S. Published Application No. 2011/275126.

FIELD

This application relates generally to a nucleic acid collection device and nucleic acid collection amount estimation method.

BACKGROUND

In the medical field, methods for diagnosing infectious diseases, genetic ailments and/or the like at the gene level are widely implemented by extracting (collecting) biological macromolecules (e.g. nucleic acids) from biological samples taken from patients and analyzing these macromolecules. In International Patent Application Publication No. WO2010/082631, a method is disclosed for collecting nucleic acids from biological samples using pipette tips to collect the nucleic acids. The pipette tips suck biological samples containing nucleic acids, pass the biological samples to a carrier which is prepared in the pipette, and cause the nucleic acids to be physically adsorbed by the carrier.

SUMMARY

With the method disclosed in International Patent Application Publication No. WO2010/082631, nucleic acids are collected by implementing a heating process on the carrier that has adsorbed the nucleic acids and then separating the nucleic acids from the carrier. Consequently, at the point in time when the nucleic acids are adsorbed by the carrier, in some cases the amount of nucleic acid collected is not known. When the amount of nucleic acid collected is small, the process until the collection amount is known becomes futile, and at that point in time, there are cases where it is impossible to again collect biological samples. In addition, when large quantities of nucleic acids are contained in the biological sample, there are times when the nucleic acids are excessively adsorbed by the carrier, resulting in clogging and, making it impossible to transition to a process for separating the nucleic acids from the carrier. Hence, a new method is needed that can estimate (predict) the quantity of nucleic acids collected even without separating the nucleic acids from the carrier.

In consideration of the foregoing, it is an object of the present invention to provide a nucleic acid collection device and a nucleic acid collection amount estimation method that can estimate the quantity of nucleic acids collected when collecting nucleic acids from a biological sample containing nucleic acids.

A nucleic acid collection device according to a first aspect of the present invention comprises:

a sucking and discharging unit for sucking in and forcing out a sample containing nucleic acids;

a collector for collecting the nucleic acids by sucking in and forcing out the sample using the sucking and discharging unit;

a pressure measurer for measuring a discharging pressure when forcing out the sample and a sucking pressure when sucking in the sample, and measuring a differential pressure that is the difference between the discharging pressure and the sucking pressure; and an estimator for estimating the collection amount of nucleic acids collected based on the measured differential pressure.

As a preferable configuration, the estimator stores in advance correlation information between the differential pressure and the nucleic acid collection amount, and estimates the collection amount of nucleic acids collected based on the differential pressure and the correlation information.

Preferably, the sucking and discharging unit forces out the sample and then sucks in the sample at high speed and further sucks in such at low speed.

A surfactant may be contained in the sample containing the nucleic acids.

A protease or a protein denaturing agent may be contained in the sample containing the nucleic acids.

Preferably, the collector is provided with a filter of a predetermined mesh size and the nucleic acids are collected by passing the sample through the filter by sucking in and forcing out the sample.

Preferably, the estimator estimates that the collection amount of the nucleic acids collected has reached a predetermined amount when the maximum value of the differential pressure is at least a predetermined value.

Preferably, the estimator estimates that the sample may not be used for further testing when the maximum value of the differential pressure is less than a predetermined value after repeatedly sucking in and forcing out with the sucking and discharging unit a predetermined number of times for the same sample.

A nucleic acid collection amount estimation method according to a second aspect of the present invention comprises:

a collection procedure for sucking in and forcing out a sample containing nucleic acids, causing the sample to pass through a collector and collecting the nucleic acids from the sample;

a pressure measuring procedure for measuring a discharging pressure when forcing out the sample and a sucking pressure when sucking in the sample, and measuring a differential pressure that is the difference between the discharging pressure and the sucking pressure; and an estimation procedure for estimating the collection amount of nucleic acids collected based on the measured differential pressure.

BRIEF DESCRIPTION OF THE DRAWINGS

A more complete understanding of this application can be obtained when the following detailed description is considered in conjunction with the following drawings, in which.

DETAILED DESCRIPTION

Exemplary embodiments described below are intended to be illustrative and not limiting. One skilled in the art could utilize a preferred embodiment in which the various elements and/or all elements therein are replaced with elements equivalent thereto, but these embodiments are included within the scope of the present invention.

Embodiment 1

Figure 1:
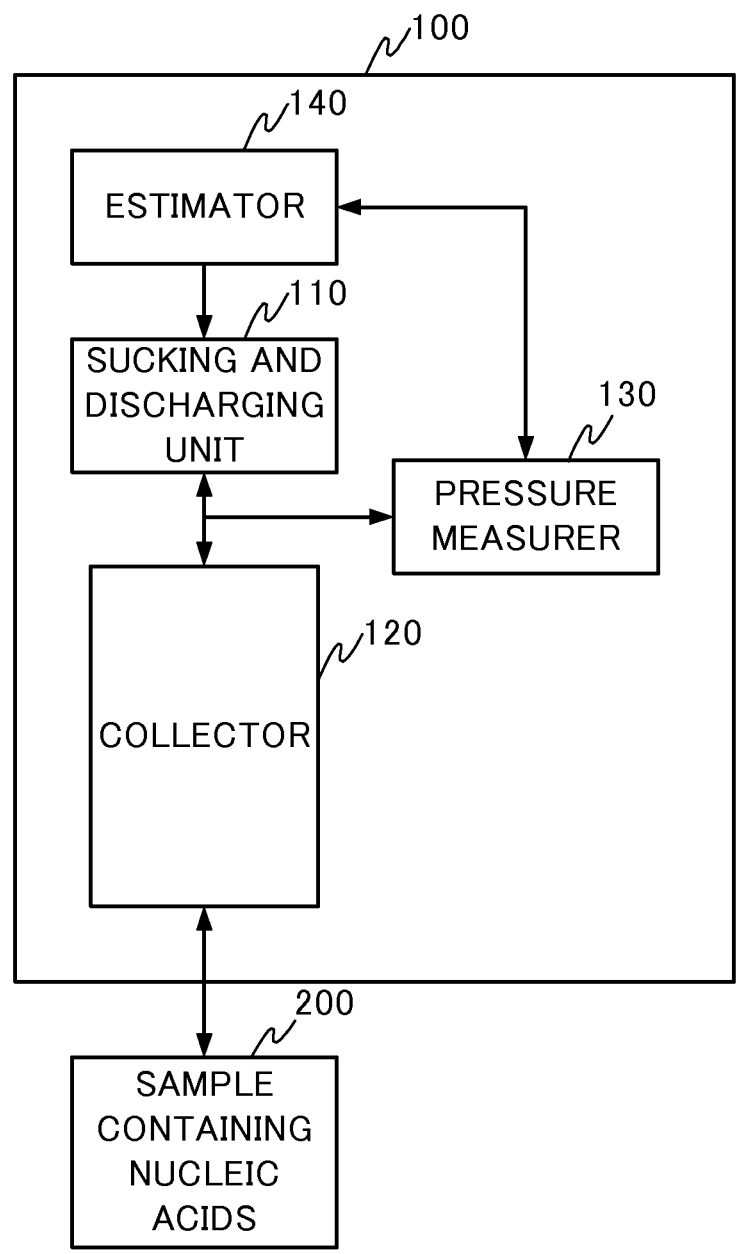
FIG. 1 is a block diagram showing an exemplary composition of a nucleic acid collection device according to an embodiment 1 of the present invention.
Figure 2:
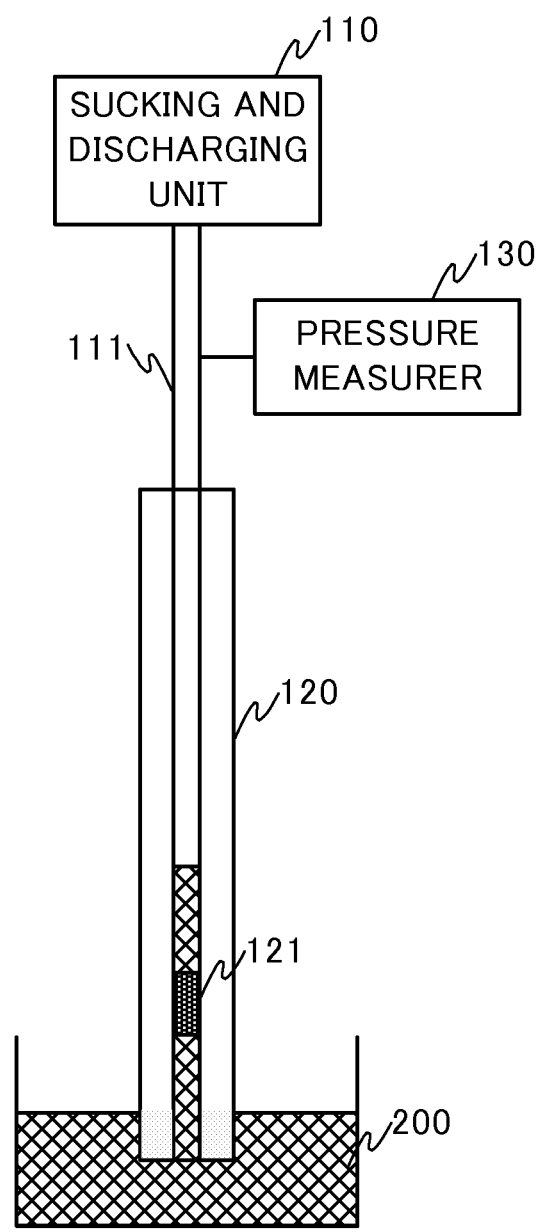
FIG. 2 is a drawing for explaining the method of sucking and discharging a sample.

The nucleic acid collection device according to an embodiment 1 of the present invention is a device for estimating the amount of nucleic acids collected when collecting nucleic acids from samples containing biological macromolecules such as nucleic acids. A nucleic acid collection device 100 according to the embodiment 1 of the present invention is composed of a sucking (suction) and discharging unit 110, a collector 120, a pressure measurer 130, an estimator 140, a tube 111, a filter 121 and/or the like, as shown in FIGS. 1 and 2.

The sucking and discharging unit 110 is composed of a pump and/or the like and sucks in and forces out samples containing nucleic acids. As shown in FIG. 2, the sucking and discharging unit 110 and the collector 120 are connected by a tube 111 and/or the like. When the sucking and discharging unit 110 sucks in and forces out, a pressure differential is created between the inside of the tube 111 and the outside of the sucking and discharging unit 110 by this sucking in and forcing out action, so the collector 120 linked to the tube 111 sucks in and forces out a sample 200 containing nucleic acids accumulated in a certain vessel.

The collector 120 is composed, for example, of a filter (carrier) for collecting a sample through physical adsorption and a nozzle for sucking in and forcing out the sample, and collects nucleic acids from a sample containing nucleic acids. The collector 120 is provided with a filter 121, as shown in FIG. 2, and causes a sample 200 containing the nucleic acids accumulated in a certain vessel to pass through the filter 121, and collects nucleic acids in the sample 200 by causing the nucleic acids in the sample 200 to be physically adsorbed by the filter 121.

Figure 3A:
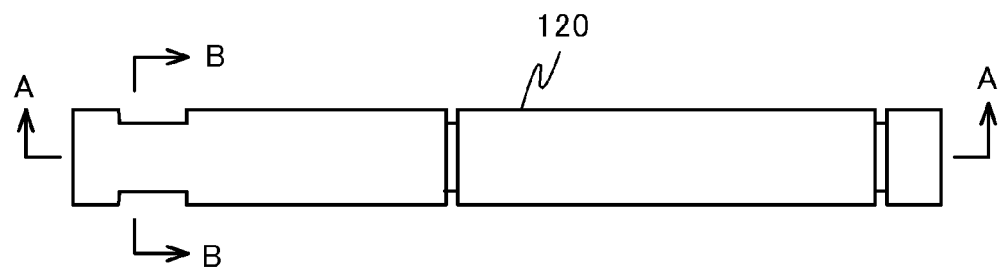
FIG. 3A is a drawing showing one example of a collector.
Figure 3B:
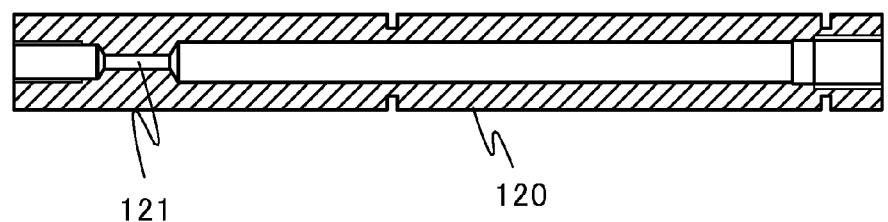
FIG. 3B is a cross-sectional view along line A-A in FIG. 3A.
Figure 3C:
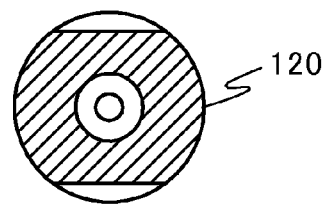
FIG. 3C is a cross-sectional view along line B-B in FIG. 3A.

FIG. 3A is a drawing showing one example of the collector 120. In addition, FIG. 3B is a cross-sectional view taken along line A-A in FIG. 3A, and FIG. 3C is a cross-sectional view taken along line B-B in FIG. 3A. As shown in these figures, the collector 120 is formed in a nozzle shape and sucks in the sample 200 containing nucleic acids from one end of the nozzle, causing the sample 200 to pass through the filter 121. Furthermore, the filter 121 collects nucleic acids from the sample 200 by adsorbing the nucleic acids when the sample 200 passes.

Returning to FIGS. 1 and 2, the pressure measurer 130 is composed of a pressure sensor and/or the like, and when the sucking and discharging unit 110 sucks in and forces out a sample, by measuring the discharging pressure and the sucking pressure measures a differential pressure, which is the difference between the discharging pressure and the sucking pressure. The pressure measurer 130 for example measures the discharging pressure at the time of forcing out and the sucking pressure at the time of sucking in by measuring the pressure near the filter 121 where collection of the nucleic acids is accomplished and the pressure inside the tube 111. When the sucking and discharging unit 110 accomplishes sucking in and forcing out, the sample 200 containing nucleic acids passes through the filter 121. When the sample 200 passes through the filter 121, the nucleic acids contained in the sample 200 are physically adsorbed by the filter 121 so that the filter 121 achieves a so-called clogged state. Furthermore, by the sucking and discharging unit 110 repeatedly sucking in and forcing out, the nucleic acids adsorbed by the filter 121 steadily increase and the filter becomes steadily more clogged. Consequently, the discharging pressure and the sucking pressure measured by the pressure measurer 130 steadily change.

Figure 4:
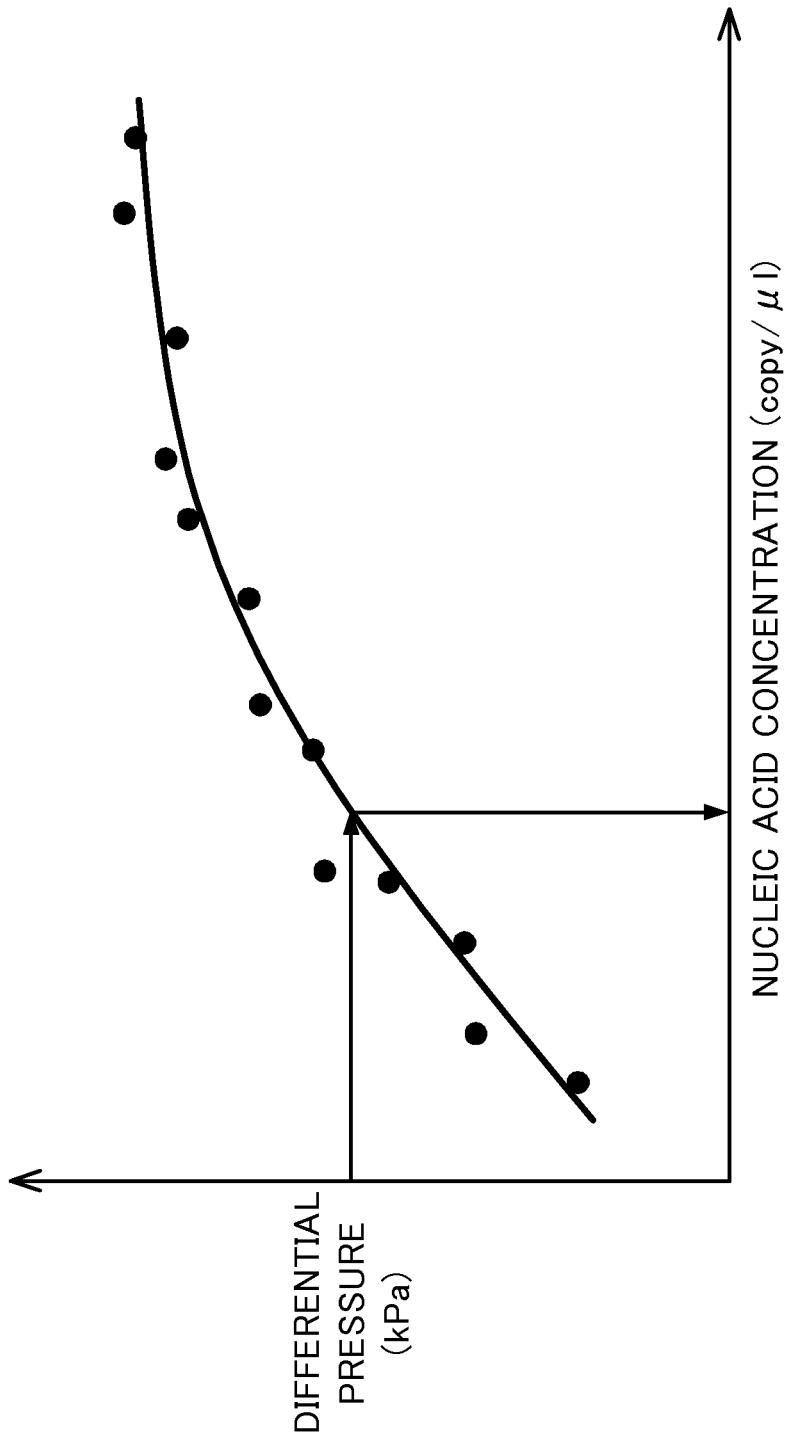
FIG. 4 is a drawing showing the correlation between the differential pressure and the nucleic acid concentration.

The estimator 140 is composed for example of a CPU (Central Processing Unit), ROM (Read Only Memory), RAM (Random Access Memory) and/or the like, and estimates the amount of nucleic acids collected by controlling the actions of the nucleic acid collection device 100 as a whole in accordance with a given operating program. The estimator 140 estimates the collection amount of nucleic acids collected by the collector 120 (filter 121) on the basis of the differential pressure that is the difference between the discharging pressure and the sucking pressure measured by the pressure estimator 130, and correlation information between the differential pressure and the nucleic acid concentration. The estimator 140 stores in advance correlation information (a correlation graph) between the differential pressure and the nucleic acid concentration (nucleic acid collection amount), such as that shown in FIG. 4. The estimator 140 estimates the nucleic acid collection amount from the nucleic acid concentration corresponding to the differential pressure by making the differential pressure between the discharging pressure and the sucking pressure as measured by the pressure measurer 130 correspond to the correlation information (correlation graph) stored in advance.

A commonly known method can be used for the method of collecting nucleic acids, the filter for collecting nucleic acids, the reagent used to collect nucleic acids and/or the like, and in addition, this content can be referenced, including the content disclosed in International Patent Application Publication No. WO2010/082631.

Figure 3D:
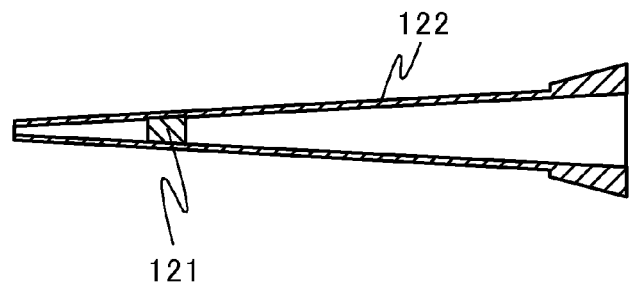
FIG. 3D is a cross-sectional view showing one example of a different collector.

FIG. 3D is a cross-sectional view showing one example of a different collector. A nozzle cap 122 shown in FIG. 3D is a member attached to an apical portion of a nozzle when the nozzle is configured to function as a collector by attaching a separated member. The nozzle cap 122, for example, is configured by a conical tube and sucks in and forces out a sample by immersing a thin tip to the sample solution. As the tip of the nozzle cap 122 is thin, even the small amount of sample may be sucked in and forced out. Furthermore, when forcing out the sample, the nozzle cap 122 has a great effect on stirring the sample. When using the nozzle cap 122, as shown in FIG. 3D for example, a filter 121 may be configured inside the nozzle cap 122.

Figure 5:
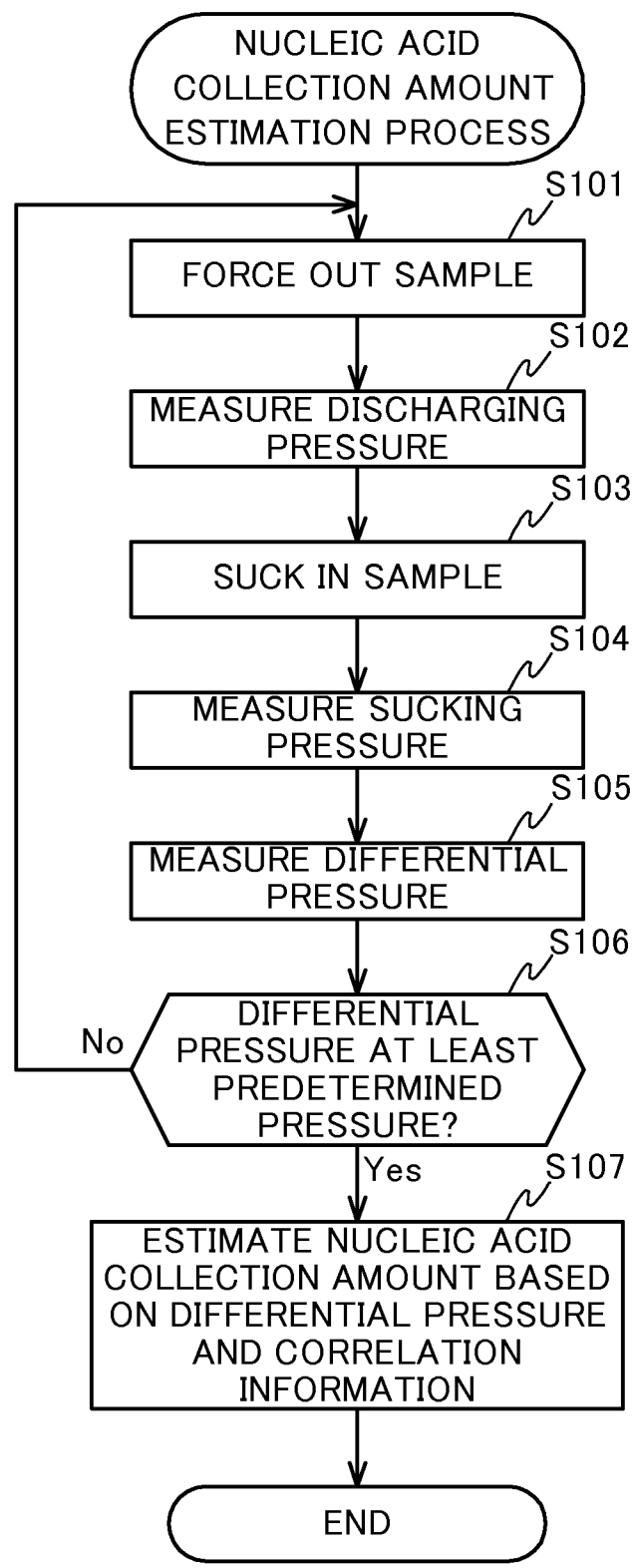
FIG. 5 is a flowchart for explaining the nucleic acid collection amount estimation process.

Below, the action of the nucleic acid collection device 100 is explained. FIG. 5 is a flowchart for explaining the process of estimating the nucleic acid collection amount accomplished by the nucleic acid collection device 100.

First, the nucleic acid collection device 100 prompts the user to accomplish nucleic acid collection and when nucleic acid collection is implemented begins the nucleic acid collection amount estimation process.

The sucking and discharging unit 110 forces out the sample 200 (step S101). When the sucking and discharging unit 110 forces out sample, the collector 120 linked by the tube 111 to the sucking and discharging unit 110 stirs the sample 200 accumulated in the vessel by forcing out the sample 200.

Figure 6:
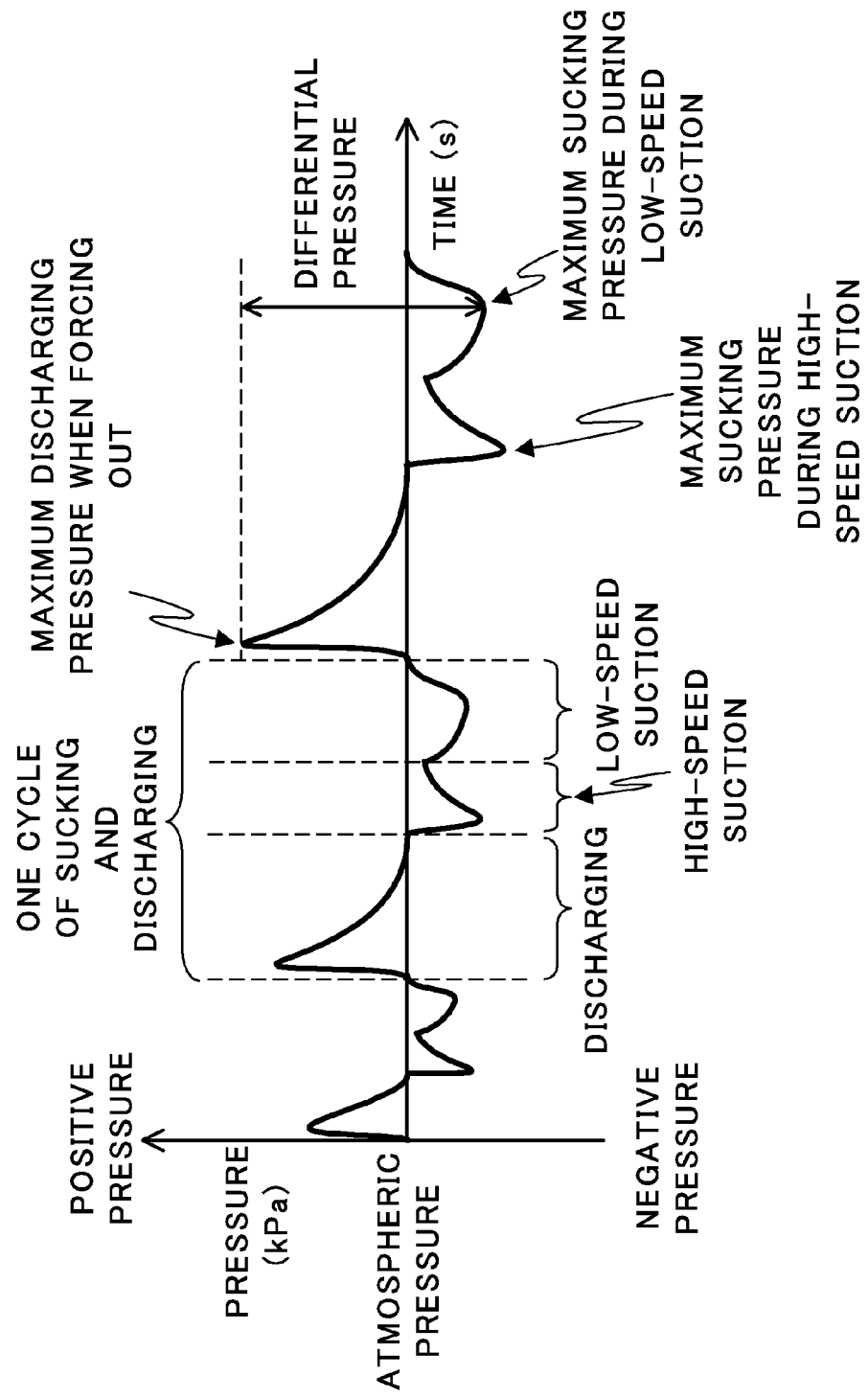
FIG. 6 is a drawing showing one example of the change in pressure with time.

The pressure measurer 130 measures the (maximum) discharging pressure when the sucking and discharging unit 110 forces out sample (step S102). FIG. 6 is a drawing showing an example of the change with time in the pressure measured by the pressure measurer 130. Calling the pressure when the sucking and discharging unit 110 forces out the sample 200 positive pressure and the pressure when the sample 200 is sucked in negative pressure, as shown in the figure the peak pressure increases with each successive iteration, and the time until the pressure returns to atmospheric pressure becomes longer. This is because the flow of the sample 200 passing through the filter 121 changes by the nucleic acids being adsorbed by the filter 121.

Next, the sucking and discharging unit 110 sucks in the sample 200 (step S103). When the sucking and discharging unit 110 sucks in, the collector 120 connected by the tube 111 to the sucking and discharging unit 110 sucks in the sample 200 stored in the vessel. By the collector 120 sucking in the sample 200, as shown in FIG. 2 the sample 200 passes through the filter 121 with which the collector 120 is provided. By the sample 200 containing nucleic acids passing through the filter 121, the filter 121 adsorbs the nucleic acids and can collect the nucleic acids. After forcing out, the sucking and discharging unit 110 accomplishes suction two times, namely high-speed suction and low-speed suction, as shown in FIG. 6. High-speed suction is suction at an instantaneous speed set at 80-200 µl/s, or preferably 90-150 µl/s, and more preferably 100-120 µl/s. In addition, low-speed suction is suction with an instantaneous speed set at 20-80 µl/s, and preferably 30-60 µl/s, and still more preferably 35-50 µl/s. In addition, one cycle of forcing out, high-speed suction and low-speed suction is considered one sucking in and forcing out cycle. As an example of this cycle, in step S103 the sucking and discharging unit 110 accomplishes high-speed suction for 0.5 second (suction of 50 µl), stops for three seconds (waits until the 50 µl has been completely sucked in), and then accomplishes low-speed suction for 2.5 seconds (sucking in 100 µl), but this example is intended to be illustrative and not limiting.

The pressure measurer 130 measures the sucking pressure when the sucking and discharging unit 110 sucks in (step S104). The reason the sucking and discharging unit 110 accomplishes two suctions, namely a high-speed suction and a low-speed suction, in step S103 is that at the time of high-speed suction there are cases when the pressure in the tube 111 (near the filter 121) is not stable. In addition, by repeating suction and discharge, there are times when the pressure after suction does not return to atmospheric pressure (i.e., deviates from atmospheric pressure), so by accomplishing low-speed suction the pressure near the filter 121 returns to atmospheric pressure. Consequently, the pressure measurer 130 can stably measure pressure and measures (maximum) sucking pressure at low-speed suction.

Figure 7:
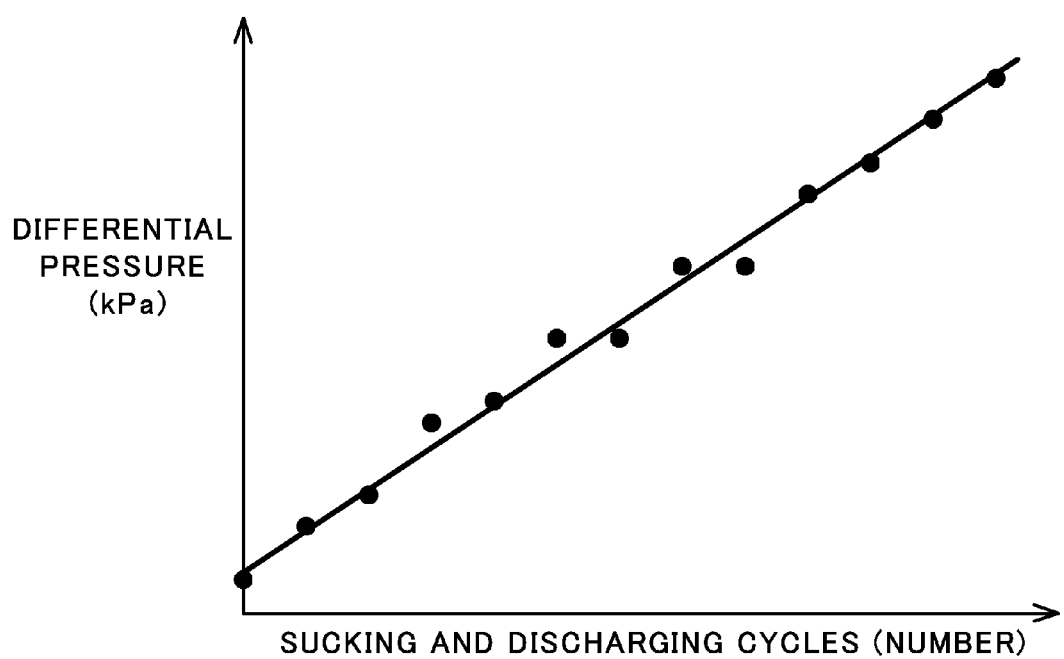
FIG. 7 is a drawing showing the correlation between the differential pressure and the sucking and discharging cycle number.

The pressure measurer 130 measures the differential pressure from the difference between the maximum discharging pressure during forcing out and the maximum sucking pressure during low-speed suction (step S105). When the sucking and discharging unit 110 repeats suction and discharge and the amount of nucleic acids adsorbed by the filter increases, the differential pressure measured by the pressure measurer 130 steadily increases, as shown in FIG. 7. The increasing trend in this case is roughly linear and increases with a trend equal to a given constant value.

Next, the estimator 140 determines whether or not the differential pressure measured by the pressure measurer 130 is at least as great as a predetermined pressure (step S106). Through this determination, it is possible to determine whether or not the amount of nucleic acid is sufficient for a PCR (Polymerase Chain Reaction) method to be accomplished after the nucleic acid collection amount estimation process. The predetermined pressure is arbitrary and varies depending on the viscosity, concentration and/or the like of the sample 200 and the mesh size (grid coarseness) of the filter 121.

When the differential pressure is not at least as great as the predetermined pressure, that is to say when the differential pressure is less than the predetermined pressure (step S106: No), the sucking and discharging unit 110 again forces out the sample 200 (step S101). By repeating the processes in steps S101 to S106, the amount of nucleic acids adsorbed by the filter 121 increases. Furthermore, these processes are repeated until the amount of nucleic acids adsorbed by the filter 121 (nucleic acid collection amount) increases and the differential pressure is at least as great as the predetermined pressure. In order for the nucleic acids to be efficiently collected, it is best to have a low process frequency, and there are some cases with low frequency in which there are just two cycles.

When the differential pressure is at least as great as the predetermined pressure (step S106: Yes), the estimator 140 estimates the nucleic acid concentration (nucleic acid collection amount) from the differential pressure measured by the pressure measurer 130 on the basis of the correlation (correlation information) between the differential pressure and the nucleic acid concentration (nucleic acid collection amount) stored in advance (step S107). Following this, the process ends. Here, there is a correlation between the differential pressure and the nucleic acid concentration (nucleic acid collection amount). This is because when the nucleic acid collection amount increases through nucleic acids being adsorbed by the filter 121 and the filter 121 becomes clogged, so the pressure when sucking in and forcing out increases. Consequently, by finding in advance the correlation between the differential pressure and the nucleic acid concentration (nucleic acid collection amount), it is possible to estimate the nucleic acid concentration (nucleic acid collection amount) from the differential pressure. In order to measure the nucleic acid concentration (nucleic acid collection amount) when the differential pressure is measured, the nucleic acids are separated (isolated) from the filter 121 and measurement of the separated nucleic acid concentration is taken through a real-time PCR method, for example. Through this, it is possible to find the correlation graph (correlation information) between the differential pressure and the nucleic acid concentration (nucleic acid collection amount), such as that shown in FIG. 4. The estimator 140 finds the differential pressure on the correlation graph (correlation information) proportionate to the differential pressure measured in step S105 and specifies the nucleic acid concentration corresponding to this differential pressure.

Through the above process, it is possible to estimate the collection amount of nucleic acids collected from samples containing nucleic acids. After the nucleic acid collection amount estimation process has been done, the nucleic acids adsorbed by the filter 121 are separated and typically measurement of DNA is accomplished through a PCR method and/or the like. In order to accomplish amplification using a polymerase chain reaction through a PCR method and/or the like, it is necessary to have a fixed amount or more of nucleic acids. Consequently, by estimating the nucleic acid collection amount from the differential pressure, it is possible to make a predictive determination (judgment) about whether the nucleic acid collection amount is an amount sufficient to accomplish a PCR method and/or the like. In addition, because the nucleic acid collection amount (nucleic acid concentration) has already been estimated, it is possible to omit a real-time PCR method or a light suction measurement method in order to measure the nucleic acid concentration. Accordingly, it is possible to collect nucleic acids from samples containing nucleic acids and efficiently determine the concentration of the nucleic acid in a short time. In addition, by using a method in which the nucleic acids are physically adsorbed and collected by a carrier, it is possible to avoid problems of the past and to efficiently and effectively collect an appropriate amount of nucleic acids.

A commonly known method can be used for the method of collecting nucleic acids, the reagent used to collect nucleic acids and/or the like, and in addition, this content can be referenced, including the content disclosed in International Patent Application Publication No. WO2010/082631.

Embodiment 2

The nucleic acid collection device 100 according to the embodiment 1 illustrates a case where the amount of nucleic acid sufficient for a PCR method was considered collected when the differential pressure was at least as great as a predetermined pressure, and nucleic acid collection then concludes. With the present preferred embodiment, a method will be described for determining that a sample containing nucleic acids may not be used for further testing when a specific pressure is not attained. Below, the nucleic acid collection amount estimation process according to an embodiment 2 is described with reference to FIG. 8. Explanation of compositions and actions that are the same as the nucleic acid collection device 100 according to the embodiment 1 are omitted here.

Figure 8:
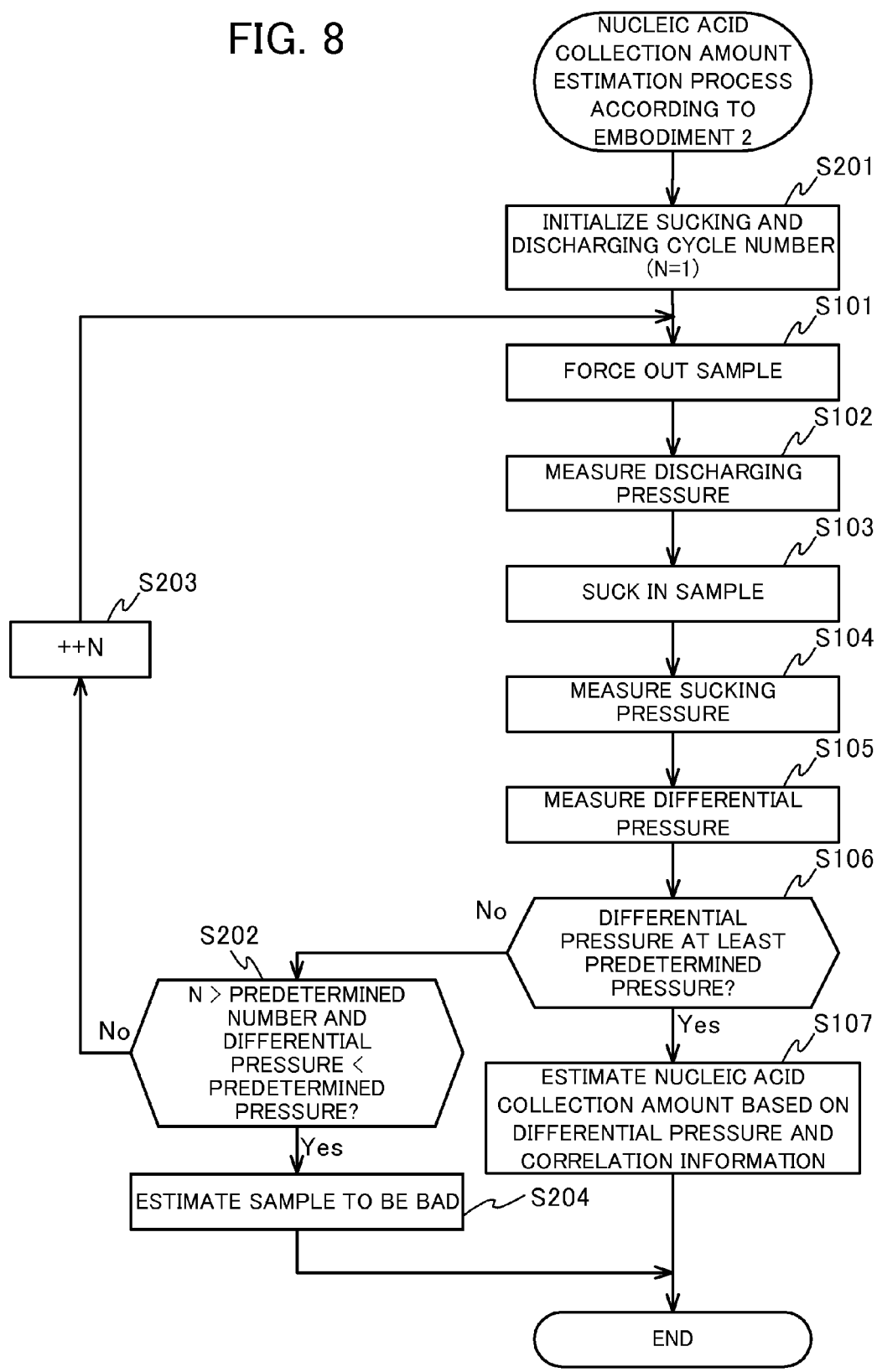
FIG. 8 is a flowchart for explaining the nucleic acid collection amount estimation process according to an embodiment 2 of the present invention.

The processes from steps S101 to S105 and S107 shown in FIG. 8 are the same as the processes from steps S101 to S105 and S107 shown in FIG. 5, so explanation is omitted. In these processes, when the differential pressure is less than a predetermined pressure, a determination is made as to whether or not the sample containing the nucleic acids may be used for further testing.

First, the estimator 140 initializes the sucking and discharging cycle count (sucking and discharging count N=1) in order to measure the sucking and discharging cycle count accomplished by the sucking and discharging unit 110 (step S201). Furthermore, after the processes in steps S101 to S105 have been accomplished, if the differential pressure is less than a predetermined pressure (step S106: No), the estimator 140 determines whether or not the sucking and discharging cycle count (N) is more than a predetermined count and the differential pressure is less than a specified pressure (step S202). Here, the predetermined cycle count and the specified pressure are a cycle count and differential pressure value that can predict that if the pressure is less than the specified pressure at the predetermined cycle count, the predetermined differential pressure will not be reached no matter how many cycles are subsequently repeated. The predetermined cycle count and specified pressure can be set through experiment and design items.

When the sucking and discharging cycle count is not greater than the predetermined cycle count and the differential pressure is at least as great as the specified pressure (step S202: No), the sucking and discharging cycle count (N) is incremented (step S203) and the sucking and discharging unit 110 again forces out the sample 200 (step S101).

When the sucking and discharging cycle count is greater than the predetermined cycle count and the differential pressure is less than the specified pressure (step S202: Yes), the estimator 140 estimates that the sample 200 containing the nucleic acids may not be used for further testing (step S204). Following this, the process concludes. When the concentration in the sample 200 is low (when the amount of nucleic acids contained in the sample 200 is sparse), the nucleic acids adsorbed by the filter 121 are sparse, so the differential pressure will not rise regardless of how many times sucking in and forcing out are accomplished. Consequently, the estimator 140 estimates that the sample 200 on which collection of nucleic acids is being conducted by accomplishing suction and discharge may not be used for further testing from which sufficient nucleic acids cannot be collected for accomplishing a PCR method and/or the like after the nucleic acid collection amount estimation process.

Through the above process, it is possible to determine (judge) in advance whether the collected amount of nucleic acids is an amount sufficient for accomplishing a PCR method and/or the like. In addition, the presence of an insufficient amount can be determined prior to a real-time PCR method or a light suction measurement method being accomplished, so it is possible to omit unnecessary measurements and to shorten measurement time.

The present invention is not limited to the above preferred embodiments, for variations and various applications thereof are possible.

Examples of target nucleic acids whose collection amount is estimated by the preferred embodiments include DNA (genome DNA, plasmid DNA, mitochondrial DNA and/or the like) and RNA (messenger RNA, transfer RNA and/or the like), but this is arbitrary as long as the length physically adsorbed by the filter 121 is a certain nucleic acid. Specific examples of nucleic acids include mammalian nucleic acids.

Prior to entering the procedure of estimating the collection amount in the preferred embodiments, it is preferable to undertake a procedure of adding a surfactant to the sample containing nucleic acids, and more preferably a non-ionic surfactant or protease. A method for using this surfactant or a method for using the protease is described in detail in US 2011275126 (A1). In addition, this is not necessary when the sample already contains a surfactant. Examples of the surfactants include Nonidet-type surfactants such as TRITON X-100, TRION X-114, Nonidet P40 and/or the like and Tween-type surfactants such as Tween 20, Tween 80 and/or the like. Examples of non-ionic surfactants include polyoxyethylene-p-isooctylphenol, polyoxyethylene sorbitan monolaurate, polyoxyethylene nonylphenyl ether, nonylphenyl polythioethoxylate and/or the like. One of these surfactants may be used alone or two or more of them may be used in combination.

Examples of the protease include proteinase K, chymotrypsin, pepsin, cathepsin D, and papain. One of these proteases may be used alone or two or more of them may be used in combination.

Preferably, in the treatment liquid in which the treatment reagent and the cell sample are mixed, the concentration of the protease is, for example, 0.5 mU/µL or more and the concentration of the surfactant is, for example, 0.1 vol % or more. By treating the cell sample under the foregoing conditions, the nucleic acid complexes can be released sufficiently. The concentration of the protease and the concentration of the surfactant are the concentrations in the treatment liquid containing the treatment reagent and the cell sample and are the concentrations in the case of assuming that the amount of the cell in the treatment liquid is $1\times10^2$ to $1\times10^9$, for example. Further, the concentration of the protease and the concentration of the surfactant are the concentrations in the treatment liquid containing the treatment reagent and the cell sample and may be the concentrations in the case of assuming that the amount of the cell sample in the treatment liquid is 50 to 100 µL and preferably 50 µL.

In the treatment liquid, the lower limit of the concentration of the protease is, for example, 0.5 mU/µL or more, preferably 1 mU/µL or more, and more preferably 2 mU/µL or more. In the treatment liquid, the upper limit of the concentration of the protease is, for example, 1 U/µL or less, and preferably 500 mU/µL or less, although it is not particularly limited. The concentration of the protease is, for example, in the range from 0.5 mU/µL to 1000 mU/µL, preferably in the range from 1 mU/µL to 1000 mU/µL, more preferably in the range from 2 mU/µL to 500 mU/µL, and particularly preferably in the range from 5 mU/µL to 15 mU/µL. With respect to the unit of protease activity (U: unit), generally, 1 U denotes the enzyme level that allows peptide to be produced corresponding to 1 µmol of tyrosine in 1 minute at 37° C. with hemoglobin being used as a substrate.

In the treatment liquid, the amount of the protease relative to $1\times10^2$ to $1\times10^9$ cells is not particularly limited. The lower limit thereof is, for example, 0.02 mU or more and preferably 0.08 mU or more, and the upper limit thereof is, for example, 100 U or less and preferably 50 U or less. Further, in the treatment liquid, the amount of the protease relative to 50 µL of the cell sample is not particularly limited. The lower limit thereof is, for example, 0.02 mU or more and preferably 0.08 mU or more, and the upper limit thereof is, for example, 100 U or less and preferably 50 U or less.

In the treatment liquid, the lower limit of the concentration of the surfactant is, for example, 0.1 vol % or more and preferably 0.2 vol % or more, although it is not particularly limited. Further, in the treatment liquid, the upper limit of the surfactant is, for example, 20 vol % or less, preferably 10 vol % or less, more preferably 5 vol % or less, and yet more preferably 2 vol % or less, although it is not particularly limited. The concentration of the surfactant is, for example, in the range from 0.1 vol % to 20 vol %, preferably in the range from 0.1 vol % to 5 vol %, more preferably in the range from 0.1 vol % to 2 vol %, and particularly preferably in the range from 0.2 vol % to 0.8 vol %.

In the treatment liquid, the amount of the surfactant relative to $1\times10^2$ to $1\times10^9$ cells is not particularly limited. The lower limit thereof is, for example, 1 femtomole ($1\times10^{-15}$ mole) or more and preferably 2 femtomoles or more, and the upper limit thereof is, for example, 200 femtomoles or less and preferably 100 femtomoles or less. Further, in the treatment liquid, the amount of the surfactant relative to 50 µL of the cell sample is not particularly limited. The lower limit thereof is, for example, 1 femtomole or more and preferably 2 femtomoles or more, and the upper limit thereof is, for example, 200 femtomoles or less and preferably 100 femtomoles or less.

In the case where the cells are eukaryotic cells (nucleated cells), the amounts of the protease and the surfactant preferably are the amounts relative to $1\times10^2$ to $1\times10^8$ cells and more preferably are the amounts relative to $1\times10^3$ to $1\times10^7$ cells. Particularly, in the case where whole blood derived cells (for example, leukocytes) out of the eukaryotic cells are used as the cells, the amounts of the protease and the surfactant preferably are the amounts relative to $5\times10^3$ to $1\times10^7$ cells and more preferably are the amounts relative to $2.5\times10^4$ to $1\times10^7$ cells. Particularly, in the case where saliva-derived cells out of the eukaryotic cells are used as the cells, the amounts of the protease and the surfactant preferably are the amounts relative to $1\times10^2$ to $1\times10^7$ cells and more preferably are the amounts relative to $1\times10^5$ to $1\times10^6$ cells. In the case where the cells are prokaryotic cells, the amounts of the protease and the surfactant preferably are the amounts relative to $1\times10^3$ to $1\times10^9$ cells and more preferably are the amounts relative to $1\times10^3$ to $1\times10^8$ cells, and, for example, the same applies to *Escherichia coli* and the like.

The concentration of the protease and the concentration of the surfactant in the treatment reagent are not particularly limited. Preferably, the concentrations are set such that the aforementioned concentrations can be obtained in the treatment liquid when the treatment reagent and the cell sample are mixed.

In addition, the specimen sample for estimating the collection amount with the preferred embodiments may contain protein denaturing agents and/or the like. Examples of protein denaturing agents include urea, β-mercaptoethanol, sodium lauryl sulfate, dithiothreitol, guanidine hydrochloride and/or the like. The concentration of protein denaturing agents in the treatment reagent is not particularly limited and for example may be 0-8 mol/mL, and preferably 1-5 mol/mL, and more preferably 1-3 mol/mL. One of these protein denaturing agents may be used alone or two or more of them may be used in combination.

Figure 9:
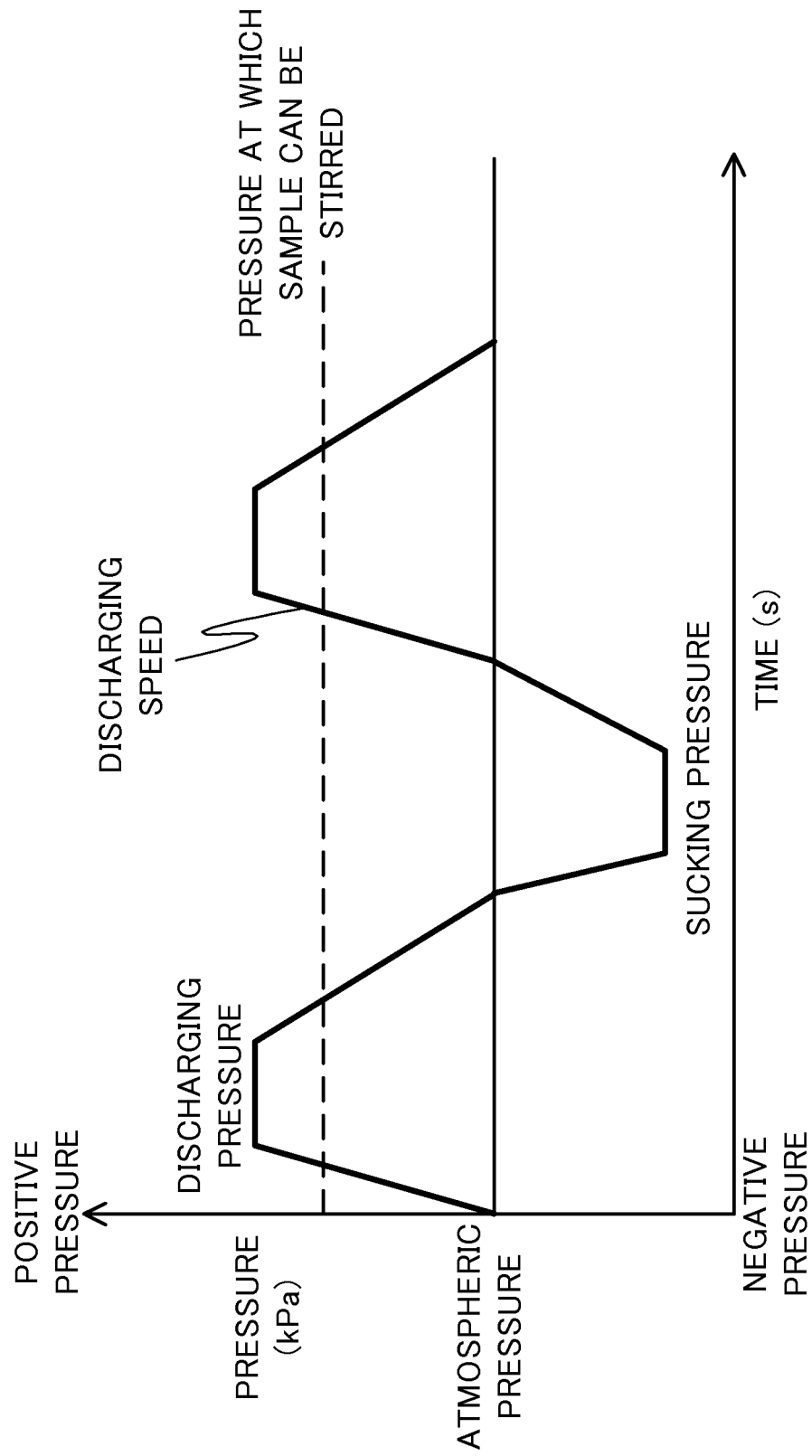
FIG. 9 is a drawing showing an example of variation in the change in pressure with time.

The speed with which the sucking and discharging unit 110 sucks in and forces out (the pressure change speed) is the speed with which the sample 200 accumulated in the vessel can be stirred, and for example is 80 µl/s or greater. In addition, as shown in FIG. 9, in order to stir the sample 200 accumulated in the vessel it is possible to set the discharging pressure (forcing out speed) at a constant or higher. In addition, the action amount and action speed of the sucking and discharging unit 110 can be set in conjunction with the mesh size (grid roughness) of the filter 121, the concentration and viscosity of the sample 200 and the length of the nucleic acids. Furthermore, the set action amount and action speed can be used to determine the differential pressure for estimating collection amounts, the action frequency for an insufficiency determination and the specified pressure.

In addition, the sucking and discharging unit 110 can, for example, accomplish high-speed suction for 0.25 to 0.625 second at an instantaneous speed of 200-80 µl/s, then stop sucking for 2-4 seconds, and then accomplish low-speed suction for 1.25 to 5 seconds at an instantaneous speed of 80-20 µl/s. The instantaneous speed, the time for accomplishing high-speed suction, the time for stopping suction and the time for accomplishing low-speed suction can be set in conjunction with the mesh size (grid roughness) of the filter 121, the concentration and density of the specimen 200 and the length of the nucleic acids.

In addition, the sucking and discharging unit 110 accomplishes suction (high-speed suction, low-speed suction), and after this can accomplish forcing out. In this case, high-speed suction→low-speed suction→discharging constitutes one cycle. The sucking and discharging cycle is arbitrary, and for example low-speed suction→high-speed suction→discharging, or discharging→low-speed suction→high-speed suction, or discharging→low-speed suction, or low-speed suction→discharging can constitute one cycle.

The shape of the collector 120 shown in FIG. 3 is one example and the shape of the collector 120 and the material thereof are arbitrary. In addition, the shape, mesh size, material and/or the like of the filter 121 provided in the collection unit 120 is arbitrary and changes depending on the length of the nucleic acids being collected.

The pressure measurer 130 can measure the pressure at an arbitrary position in the tube 111. In addition, the pressure measurer 130 can measure the pressure at an arbitrary position (for example, the end surface of the collector 120, or the end surface of the filter 121) outside the tube 111. In addition, the shape and material of the tube 111 are arbitrary.

The pressure for determining the end of sucking in and forcing out, the pressure for determining insufficient samples and the sucking and discharging cycle count are arbitrary and change depending on the concentration of the sample 200, the mesh size of the filter 121, the differential pressures (discharging pressure, sucking pressure), the pressure change speed and/or the like.

The estimator 140 can estimate the nucleic acid collection amount based on not just the maximum value of the differential pressure measured by the pressure measurer 130 but also, for example, the average value of the differential pressure, the median value of the differential pressure and/or the like. In addition, the estimator 140 can also estimate the nucleic acid collection amount using the change ratio or time in going from the peak differential pressure to 0, as shown in FIG. 6.

Example

Below, the present invention is explained concretely using an example, but this is intended to be illustrative and not limiting.

(Correlation Between Differential Pressure and Nucleic Acid Concentration).

What kind of correlation there is between the differential pressure and the nucleic acid concentration was confirmed.

A reagent 2 (10 mM Tris, 1% Nonidet P40, 0.05% sodium azide aqueous solution) was added to a reagent 1 (2 U protease K, 10 mM Tris, 5 mM calcium chloride, 30% glycerol, 1% Nonidet P40, 0.05% sodium azide aqueous solution) to produce a mixed reagent. Next, a biological sample formed by adding the mixed reagent to a human blood sample was accumulated in a certain vessel and this biological sample was sucked in and forced out. In order to collect nucleic acids from the biological sample, a collector having the shape shown in FIGS. 3A to 3C was used. As a filter for collecting the nucleic acids, a PET mesh sheet TN255 (made by Sanplatec Corporation) having a mesh size (opening) of 60 μm was used. In addition, as a pump for sucking in and forcing out, a 0.5 ml Gastight® 1750 (made by Hamilton Co.) was used.

The biological sample was sucked in and forced out, and while measuring the differential pressure between the discharging pressure and the sucking pressure the nucleic acids contained in the biological sample were adsorbed by the filter. The filter that adsorbed the nucleic acids was washed with a reagent 3 (200 mM calcium chloride, 0.05% sodium azide aqueous solution) and a reagent 4 (10 mM Tris, 1 mM ethylenediaminetetraacetic acid (EDTA), 0.05% sodium azide aqueous solution), and then the filter was heated to 90° C. for 10 minutes in the reagent 4 and through this the nucleic acids were eluted (isolated) from the filter. Then, the concentration of the nucleic acids eluted from the filter was measured using a real-time PCR method.

Figure 10:
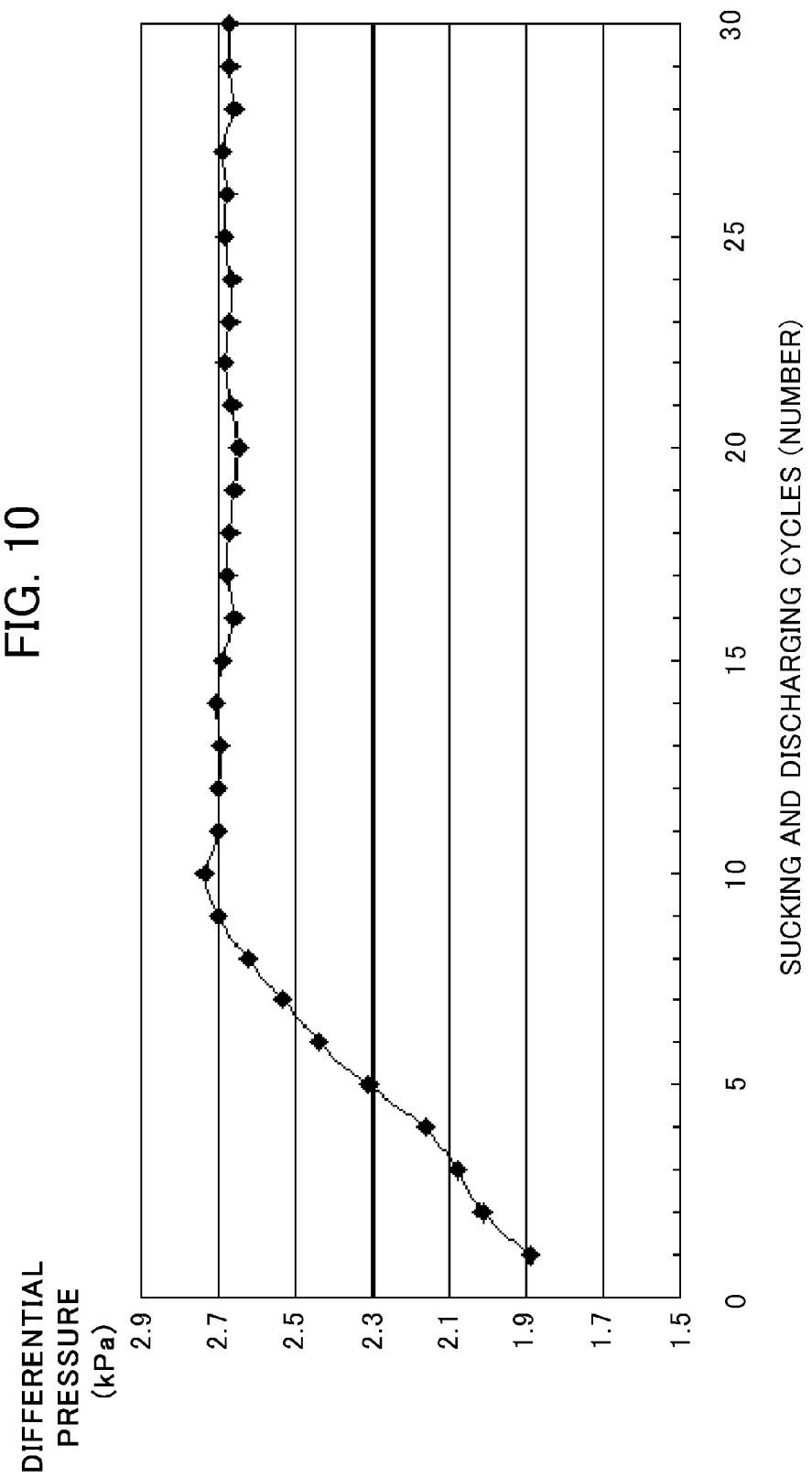
FIG. 10 is a drawing showing the relationship between the differential pressure and the sucking and discharging cycle number.

FIG. 10 is a drawing showing the relationship between the differential pressure and the sucking and discharging cycle count. As shown in this figure, by repeatedly sucking in and forcing out, the differential pressure increases. Consequently, it was found that the differential pressure (discharging pressure, sucking pressure) changes by the nucleic acids being adsorbed by the filter.

Figure 11:
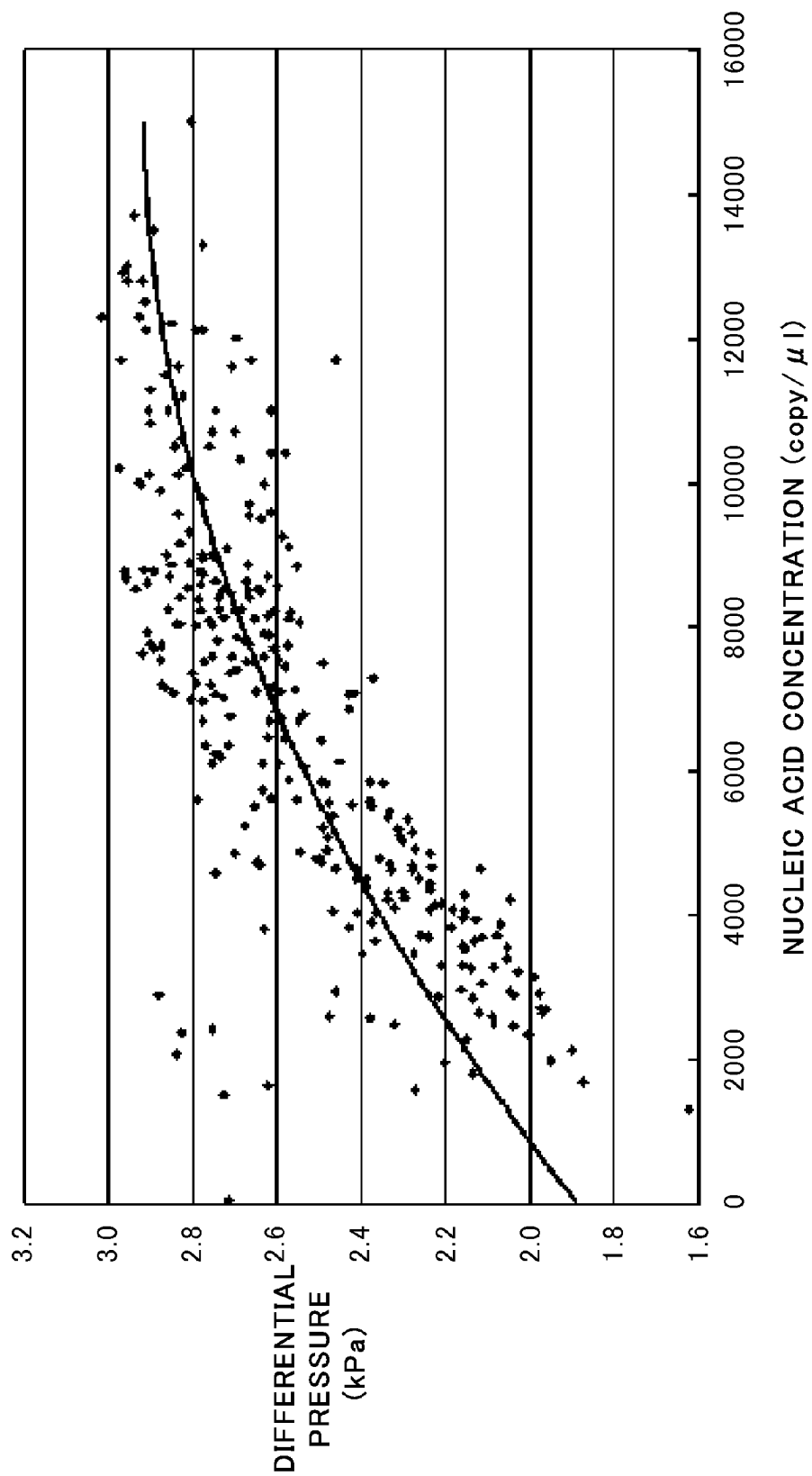
FIG. 11 is a drawing showing the relationship between the differential pressure and the nucleic acid concentration.

FIG. 11 is a drawing showing the relationship between the differential pressure and the nucleic acid concentration. As shown in this figure, it was learned that the nucleic acid concentration (nucleic acid collection amount) increases as the differential pressure increases. Furthermore, when the differential pressure is 2 kPa or less, the nucleic acid concentration is estimated at 1000 copy/μl or less, and it was found that there is a possibility that measurement through the PCR method and/or the like cannot be accomplished with certainty. When the differential pressure is 2.4 kPa or greater, the nucleic acid concentration is estimated at 4000 copy/μl, so it was found that measurements using the PCR method and/or the like can be accomplished with certainty.

On the other hand, when the differential pressure exceeds 3 kPa, there is a possibility that clogging of the carrier could result from excessive nucleic acid adsorption, and when a clogged state occurs, sucking in and forcing out of the solution in the next process is not accomplished and collecting nucleic acids from the carrier becomes impossible. Accordingly, when the differential pressure is 2.8 kPa, the nucleic acid concentration is estimated at 10000 copy/μl so when the differential pressure is 2.8 kPa or greater, sucking in and forcing out were halted so that it was possible to prevent in advance clogging caused by excessive nucleic acid adsorption when moving to the next process.

Having described and illustrated the principles of this application by reference to one or more preferred embodiments, it should be apparent that the preferred embodiments may be modified in arrangement and detail without departing from the principles disclosed herein and that it is intended that the application be construed as including all such modifications and variations insofar as they come within the spirit and scope of the subject matter disclosed herein.

What is claimed is:

1. A nucleic acid collection device comprising:
   a sucking and discharging unit for sucking in and forcing out a sample containing nucleic acids;
   a collector for collecting the nucleic acids by sucking in and forcing out the sample using the sucking and discharging unit;
   a pressure measurer for measuring a discharging pressure when forcing out the sample and a sucking pressure when sucking in the sample, and measuring a differential pressure that is the difference between the discharging pressure and the sucking pressure; and
   an estimator for estimating the collection amount of nucleic acids collected based on the measured differential pressure.

2. The nucleic acid collection device of claim 1, wherein the estimator stores in advance correlation information between the differential pressure and the nucleic acid collection amount, and estimates the collection amount of nucleic acids collected based on the differential pressure and the correlation information.

3. The nucleic acid collection device of claim 1, wherein the sucking and discharging unit forces out the sample and then sucks in the sample at high speed and further sucks in such at low speed.

4. The nucleic acid collection device of claim 2, wherein the sucking and discharging unit forces out the sample and then sucks in the sample at high speed and further sucks in such at low speed.

5. The nucleic acid collection device of claim 1, wherein a surfactant is contained in the sample containing the nucleic acids.

6. The nucleic acid collection device of claim 1, wherein a protease or a protein denaturing agent is contained in the sample containing the nucleic acids.

7. The nucleic acid collection device of claim 1, wherein the collector is provided with a filter of a predetermined mesh size and the nucleic acids are collected by passing the sample through the filter by sucking in and forcing out the sample.

8. The nucleic acid collection device of claim 2, wherein the collector is provided with a filter of a predetermined mesh size and the nucleic acids are collected by passing the sample through the filter by sucking in and forcing out the sample.

9. The nucleic acid collection device of claim 3, wherein the collector is provided with a filter of a predetermined mesh size and the nucleic acids are collected by passing the sample through the filter by sucking in and forcing out the sample.

10. The nucleic acid collection device of claim 4, wherein the collector is provided with a filter of a predetermined mesh size and the nucleic acids are collected by passing the sample through the filter by sucking in and forcing out the sample.

11. The nucleic acid collection device of claim 1, wherein the estimator estimates that the collection amount of the nucleic acids collected has reached a predetermined amount when the maximum value of the differential pressure is at least a predetermined value.

12. The nucleic acid collection device of claim 3, wherein the estimator estimates that the collection amount of the nucleic acids collected has reached a predetermined amount when the maximum value of the differential pressure is at least a predetermined value.

13. The nucleic acid collection device of claim 4, wherein the estimator estimates that the collection amount of the nucleic acids collected has reached a predetermined amount when the maximum value of the differential pressure is at least a predetermined value.

14. The nucleic acid collection device of claim 7, wherein the estimator estimates that the collection amount of the nucleic acids collected has reached a predetermined amount when the maximum value of the differential pressure is at least a predetermined value.

15. The nucleic acid collection device of claim 1, wherein the estimator estimates that the sample may not be used for further testing when the maximum value of the differential pressure is less than a predetermined value after repeatedly sucking in and forcing out with the sucking and discharging unit a predetermined number of times for the same sample.

16. The nucleic acid collection device of claim 3, wherein the estimator estimates that the sample may not be used for further testing when the maximum value of the differential pressure is less than a predetermined value after repeatedly sucking in and forcing out with the sucking and discharging unit a predetermined number of times for the same sample.

17. The nucleic acid collection device of claim 4, wherein the estimator estimates that the sample may not be used for further testing when the maximum value of the differential pressure is less than a predetermined value after repeatedly sucking in and forcing out with the sucking and discharging unit a predetermined number of times for the same sample.

18. The nucleic acid collection device of claim 7, wherein the estimator estimates that the sample may not be used for further testing when the maximum value of the differential pressure is less than a predetermined value after repeatedly sucking in and forcing out with the sucking and discharging unit a predetermined number of times for the same sample.

19. The nucleic acid collection device of claim 11, wherein the estimator estimates that the sample may not be used for further testing when the maximum value of the differential pressure is less than a predetermined value after repeatedly sucking in and forcing out with the sucking and discharging unit a predetermined number of times for the same sample.

20. A nucleic acid collection amount estimation method comprising:
   a collection procedure for sucking in and forcing out a sample containing nucleic acids, causing the sample to pass through a collector and collecting the nucleic acids from the sample;
   a pressure measuring procedure for measuring a discharging pressure when forcing out the sample and a sucking pressure when sucking in the sample, and measuring a differential pressure that is the difference between the discharging pressure and the sucking pressure; and
   an estimation procedure for estimating the collection amount of nucleic acids collected based on the measured differential pressure.

* * * * *